United States Patent
Feldman et al.

(10) Patent No.: US 11,421,270 B2
(45) Date of Patent: Aug. 23, 2022

(54) SCREENING OF NUCLEIC ACID SEQUENCE VARIATIONS VIA RANDOM LOADING OF OPTICALLY-ENCODED PARTICLES

(71) Applicants: THE BROAD INSTITUTE, INC., Cambridge, MA (US); MASSACHUSETTS INSTITUTE OF TECHNOLOGY, Cambridge, MA (US)

(72) Inventors: David Feldman, Redmond, WA (US); Daniel Sazer, Newton, MA (US); Paul Blainey, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 506 days.

(21) Appl. No.: 15/754,984

(22) PCT Filed: Aug. 25, 2016

(86) PCT No.: PCT/US2016/048687
§ 371 (c)(1),
(2) Date: Feb. 23, 2018

(87) PCT Pub. No.: WO2017/035347
PCT Pub. Date: Mar. 2, 2017

(65) Prior Publication Data
US 2020/0232009 A1    Jul. 23, 2020

Related U.S. Application Data

(60) Provisional application No. 62/209,709, filed on Aug. 25, 2015.

(51) Int. Cl.
*C12Q 1/686* (2018.01)
*B01L 3/00* (2006.01)
*G01N 21/25* (2006.01)
*G01N 21/64* (2006.01)

(52) U.S. Cl.
CPC ........ *C12Q 1/686* (2013.01); *B01L 3/502761* (2013.01); *G01N 21/253* (2013.01); *B01L 2300/0829* (2013.01); *C12Q 2561/113* (2013.01); *C12Q 2563/155* (2013.01); *C12Q 2563/159* (2013.01); *C12Q 2565/514* (2013.01); *G01N 21/6452* (2013.01)

(58) Field of Classification Search
CPC .............................. C12Q 1/686; B01L 3/5027
See application file for complete search history.

(56) References Cited

U.S. PATENT DOCUMENTS

| | | | |
|---|---|---|---|
| 2001/0038070 A1 | 11/2001 | Hausch et al. | |
| 2005/0255600 A1* | 11/2005 | Padmanabhan | G01N 15/1484 436/63 |
| 2007/0178604 A1 | 8/2007 | Watkins et al. | |
| 2009/0029364 A1 | 1/2009 | Zirwes et al. | |
| 2014/0051087 A1 | 2/2014 | Makrigiorgos et al. | |
| 2014/0080717 A1* | 3/2014 | Li | C12Q 1/6846 506/2 |
| 2014/0212881 A1* | 7/2014 | Handique | C12Q 1/6841 435/6.12 |
| 2015/0292988 A1* | 10/2015 | Bharadwaj | B01L 3/502761 506/27 |

FOREIGN PATENT DOCUMENTS

| | | | |
|---|---|---|---|
| WO | 2011053241 A1 | 5/2011 | |
| WO | WO-2015017866 A1 * | 2/2015 | ............. C12N 15/85 |

OTHER PUBLICATIONS

International Search Report and Written Opinion for PCT International Application No. PCT/US2016/048687, dated Nov. 18, 2016, 9 pages.
Dressman, et al., "Transforming Single DNA Molecules Into Fluorescent Magnetic Particles for Detection and Enumeration of Genetic Variations", Proc Natl Acad Sci USA, vol. 100, Jul. 11, 2003, 8817-22.
Nickitas-Etienne, "International Preliminary Report on Patentability for PCT Application No. PCT/US2016/048687", dated Mar. 8, 2018, 1-13.
"Extended European Search Report for European Patent Application No. 20166741.7", dated Sep. 28, 2020, 11 pages.
Brouzes, et al., "Droplet Microfluidic Technology for Single Cell High-Throughput Screening", Proceedings of the National Academy of Sciences (PNAS). vol. 106, No. 34, Aug. 25, 2009 (Aug. 25, 2009), pp. 14195-14200, XP055446345.
Gungun, et al., "Magnetofluidic Platform for Multidimensional Magnetic and Optical Barcoding of Droplets", Lab on a Chip, vol. 15, No. 1, Jan. 1, 2015 (Jan. 1, 2015), pp. 216-224, XP055731620, ISSN: 1473-0197, DOI: 10.1039/C4LC01160K.

(Continued)

*Primary Examiner* — Angela M. Bertagna
*Assistant Examiner* — Carolyn L Greene
(74) *Attorney, Agent, or Firm* — F. Brent Nix, Esq.; Johnson, Marcou, Isaacs & Nix, LLC

(57) ABSTRACT

Embodiments disclosed herein provide reagents and methods for high-throughput screening of nucleic acid sequence variations in nucleic acid containing specimens. Nucleic acid specimens to be screened are loaded into separate discrete volumes. Optically encoded particles are used to deliver primers to amplify one or more sequences comprising the nucleic acid sequence variation. The optically encoded particles may be delivered to the discrete volumes randomly resulting in a random combination of optically encoded particles in each well, or a unique combination of optically encoded particles may be specifically assigned to each discrete volume. The observable combination of optically encoded particles may then be used to identify each discrete volume.

23 Claims, 7 Drawing Sheets

(56) References Cited

OTHER PUBLICATIONS

Klein, et al., "Droplet Barcoding for Single-Cell Transcriptomics Applied to Embryonic Stem Cells", Cell, vol. 161, No. 5, May 1, 2015 (May 1, 2015), pp. 1187-1201, XP055731640, Amsterdam, NL ISSN: 0092-8674, DOI: 10 .1016/j.ce 11 . Apr. 2015. 044, 16 pages.

Shembekar, et al., "Droplet-Based Microfluidics in Drug Discovery, Transcriptomics and High-Throughput Molecular Genetics", Lab on a CHIP, vol. 16, No. 8, Mar. 18, 2016 (Mar. 18, 2016), pp. 1314-1331, XP055451515, ISSN: 1473-0197, DOI: 10.1039/C6LC00249H.

Xing-Hu, et al., "On-Demand Preparation of Quantum Dot-Encoded Microparticles using a Droplet Microfluidic System", Lab on a Chip, vol. 11, No. 15, Jan. 1, 2011 (Jan. 1, 2011), p. 2561, XP055186167, 8 pages.

Zhao, et al., "Microfluidic Generation of Multifunctional Quantum Dot Barcode Particles", Journal of the American Chemical Society, vol. 133, No. 23, Jun. 15, 2011 (Jun. 15, 2011), pp. 8790-8793, XP055731601, US ISSN: 0002-7863, DOI: 10.1021/ia200729w.

Zhao, et al., "Microfluidic Generation of Multifunctional Quantum Dot Barcode Particles", Supporting Information; Journal of the American Chemical Society, vol. 133, No. 23, Jun. 15, 2011 (Jun. 15, 2011), pp. 8790-8793, XP055731718, US ISSN: 0002-7863, DOI: 10.1021/ja200729w.

\* cited by examiner

SCREENING OF NUCLEIC ACID SEQUENCE VARIATIONS VIA RANDOM LOADING OF OPTICALLY-ENCODED PARTICLES

REFERENCE TO RELATED APPLICATIONS

This application is a 35 U.S.C. § 371 national stage application of International Patent Application No. PCT/US2016/048687 filed Aug. 25, 2016, and entitled "Screening of Nucleic Acid Sequence Variations via Random Loading of Optically-Encoded Particles," and claims priority to U.S. Provisional Application No. 62/209,709 filed Aug. 25, 2015 and entitled "Screening of Nucleic Acid Sequence Variations via Random Loading of Optically-Encoded Particles," the complete disclosure of which is hereby fully incorporated herein by reference.

TECHNICAL FIELD

The subject matter disclosed herein is generally directed to multiplex methods for screening nucleic acid sequence variations. Specifically, the subject matter disclosed herein is directed to systems and methods that use optically encoded particles to enable direct correlation between nucleic acid sequence variations and observable characteristics of cells and other nucleic acid containing specimens.

BACKGROUND

Advances in genome engineering now allow independent modification of a uniform genetic background across tens of thousands of loci. The resulting libraries of genotypes provides a tremendous resource for understanding the effects of genetic interactions to disease models, stem cell differentiation, and fundamental cellular processes. A primary challenge in employing large libraries of edited cells are isolation and validation of clonal cell lines, without which only FACS-compatible and positive selection phenotypes can be assessed. Traditionally, isogenic cell lines are generated by picking individual cells and culturing in multi-well plates before sequencing, requiring two weeks of labor per isogenic line. Accordingly, what is needed are methods and systems for highly multiplex screening that reduce the cost and time needed to screen large cell libraries.

SUMMARY

In one aspect, the embodiments described herein are directed to methods for multiplex screening of nucleic acid sequence variations in one or more nucleic acid containing specimens. The nucleic acid sequence variations may include natural sequence variability, variations in gene expression, engineered genetic perturbations, or a combination thereof. The nucleic acid containing specimen may be cellular or acellular. The nucleic acid containing specimens are loaded into individual discrete volumes. A single solution comprising a set of optically encoded particles is then dispensed across all discrete volumes resulting in delivery of a combination of optically encoded particles to each discrete volume. The optically encoded particles are associated with one or more primers of a same primer type, e.g. forward or reverse primer, that will amplify one or more target sequences comprising the nucleic acid sequence variation. Each primer in turn encodes a particle identifier which identifies the type of optically encoded particle it is associated with. The combination of optically encoded particles is detected in each discrete volume thereby allowing each discrete volume to be identified by the observed combination of optically encoded particles. In addition, optical assessments, such as observation of cell phenotype, may be conducted on each discrete volume. Amplicons comprising the one or more target sequences are generated in each discrete volume using the one or more primers delivered to each discrete volume. The generated amplicons are then sequenced, the amplicon sequence information including the primer particle identifier. The amplicon sequence information may then be clustered by sequence similarity of the one or more target sequences such that all amplicon sequences having the same nucleic acid sequence variation are aligned. The discrete volume from which a given nucleic acid variation originated is then determined by matching the particle identifiers from the aligned sequences to the discrete volume where a combination of optically encoded particles corresponding to the particle identifiers was detected, thereby allowing optical assessments of the nucleic acid containing specimens to be correlated to sequence information.

These and other aspects, objects, features, and advantages of the example embodiments will become apparent to those having ordinary skill in the art upon consideration of the following detailed description of illustrated example embodiments.

DETAILED DESCRIPTION OF THE EXAMPLE EMBODIMENTS

Overview

Figure 1:
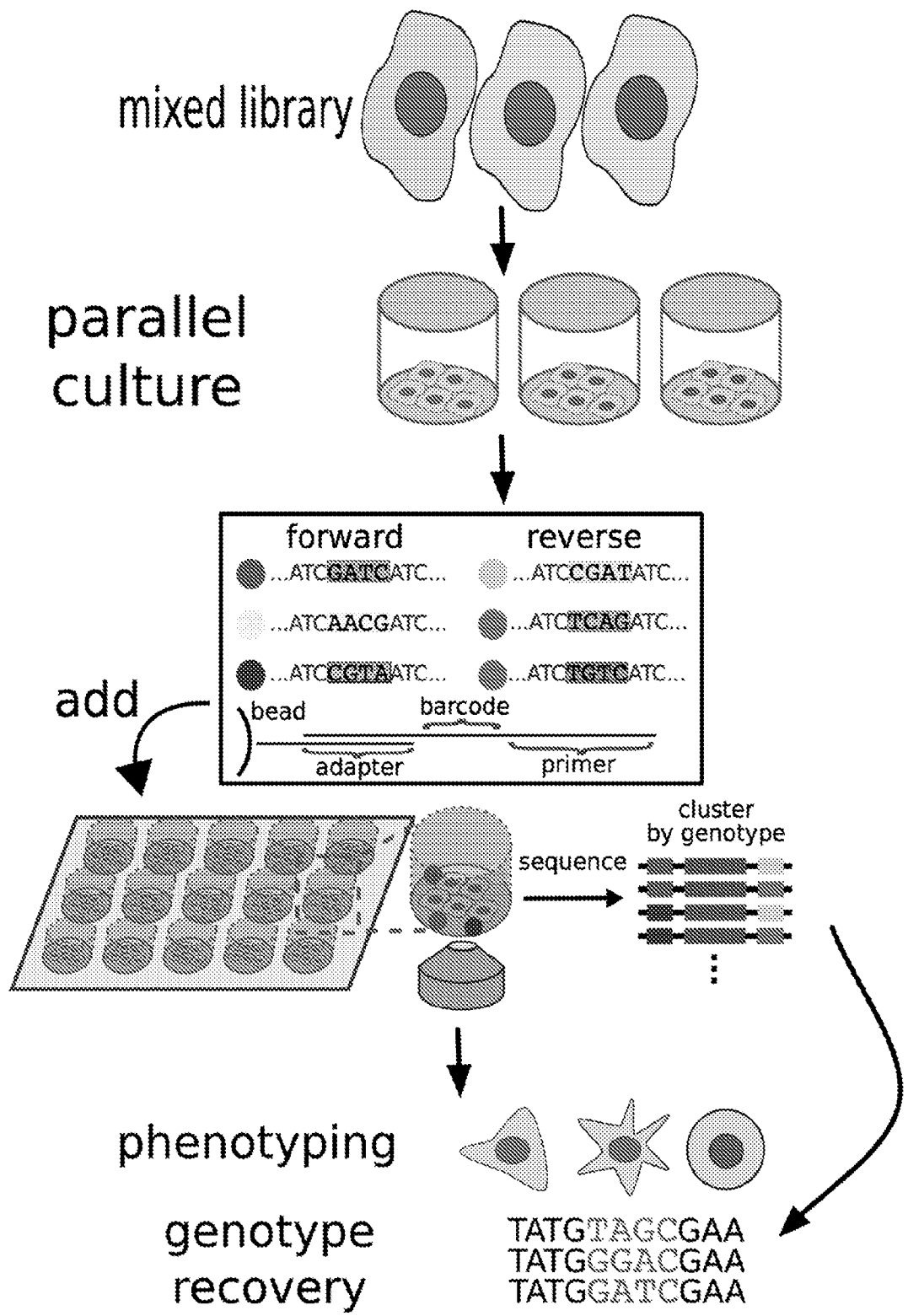
FIG. 1 is a diagram providing an overview of a method for screening of nucleic acid sequence variations, in accordance with certain example embodiments.

Embodiments disclosed herein provide reagents and methods for high-throughput screening of nucleic acid sequence variations in nucleic acid containing specimens. Nucleic acid specimens to be screened are loaded into separate discrete volumes. Optically encoded particles are used to deliver primers to amplify one or more sequences comprising the nucleic acid sequence variation. The optically encoded particles may be delivered to the discrete volumes randomly resulting in a random combination of optically encoded particles in each well, or a unique combination of optically encoded particles may be specifically assigned to each discrete volume. The observable combination of optically encoded particles may then be used to identify each discrete volume. A portion of each primer sequence, termed the particle identifier, functions as an identifier of the type of optically encoded particle with which the primer is associated. Optical assessments, such as phenotype, may then be made and recorded for each discrete volume. To correlate the optical assessment with nucleic acid sequence variation, nucleic acid amplification is conducted in each discrete volume using the primers delivered to that discrete volume. The resulting amplicon incorporates primer sequence information including the particle identifier. Sequencing reads of the amplicons are aligned according to similarity of the one or more target sequences. The particle identifier incorporated in each sequencing read identifies the optically encoded particle with which it was associated in the discrete volume. The combination of particle identifiers in a set of aligned sequences will indicate that the nucleic acid sequence variation originated from the discrete volume receiving that particular combination of optically encoded particles. The optical assessment can then be correlated with the nucleic acid sequence variation by identifying the discrete volume that displayed the same combination of optically encoded particles.

Nucleic Acid Containing Specimens

The embodiments disclosed herein may be used to detect nucleic acid sequence variation in a nucleic acid containing specimen. The nucleic acid sequence variations detected may include natural sequence variability, gene expression variability, engineered genetic perturbations, or a combination thereof. The nucleic acid containing specimen may be cellular or acellular. For example, a cellular specimen may include an intact cell from cell culture, tissue, or biopsy. An acellular sample may include, but is not limited to, a cellular extract, a cellular fraction or sub-fraction (including nuclear or cytoplasmic fractions or isolated organelles), a cell-free system, and/or an in vitro solution, including but not limited to, an aliquot from an assay screen, probe or experimental solution or reaction. The nucleic acid containing specimen may comprise RNA, DNA, or a combination thereof. In certain example embodiments, the nucleic acid containing specimen is a single cell. In certain other example embodiments, the nucleic acid containing specimen is a population of cells. In certain example embodiments, the cells are clonal cells of a uniform genetic background. In certain example embodiments, the nucleic acid containing specimens may be exposed to different physical parameters, such as temperature and pressure, or different chemical perturbations, such as exposure to different types or concentrations of a therapeutic agent, contacted with one or more infections agents, or a combination thereof.

Discrete Volumes

The nucleic acid containing specimens to be screened are loaded in separate discrete volumes. As used herein, a "discrete volume" or "discrete space" may refer to a container, receptacle, or other defined volume or space that can be defined by properties that prevent and/or inhibit migration of molecules, particles and/or nucleic acid containing specimens. For example, a discrete volume or space may be defined by physical properties such as walls of a discrete well, tube, or surface of a droplet which may be impermeable or semipermeable. The discrete volume or space may also refer to a reaction unit or region within a larger volume, where that region is not defined by walls but rather is defined spatially by location within the larger volume, wherein that region is at least large enough to contain at least one, preferably two or more, optically encoded particles of the invention. For example, the discrete volume or space may be chemically defined, diffusion rate limited defined, electromagnetically defined, or optically defined, or any combination thereof that can contain a nucleic acid containing specimen and at least one optically encoded particle. By "diffusion rate limited" is meant volumes or spaces that are only accessible to certain species or reactions because diffusion constraints that would effectively limit the migration of a particular molecule, particle, or nucleic acid containing specimen from one discrete volume to another. By "chemically defined" is meant a volume or space where only certain molecules, particles, or nucleic acid containing specimens can exist because of their chemical or molecular properties. For example, certain gel beads may exclude certain molecules, particles, or nucleic acid containing specimens from entering the beads but not others by surface charge, matrix size, or other physical property of the gel bead. By "electro-magnetically defined" is meant volumes or spaces where the electro-magnetic properties of certain molecules, particles, or cells may be used to define certain volumes or spaces. For example, by capturing magnetic particles within a magnetic field or directly by magnets. By "optically defined" is meant volumes or spaces that may be defined by illuminating the volume or space with visible, ultraviolet, infrared, or other wavelengths of light such that only target molecules within the defined space or volume are detected.

In some embodiments, the discrete volumes may be delineated as an area across a 2-D surface, such as the surface of a reaction chamber, microfluidics circuit or microwell, or may be a user-defined volume within a 3-D vessel or sample. The discrete volumes may be of any size suitable for maintaining the nucleic acid containing specimen and for optical imaging of the contents of the discrete volume. In certain example embodiments the discrete volumes are suitable for the culturing of live cells. In certain example embodiments, the discrete volume may be the wells of a standard microwell plate, such as 6 well, 24 well, 96 well, 384 well, or 1,536 well plate. The microwell plate may be made of any material suitable for imaging of the discrete volumes using the imaging modalities described herein.

Figure 2:
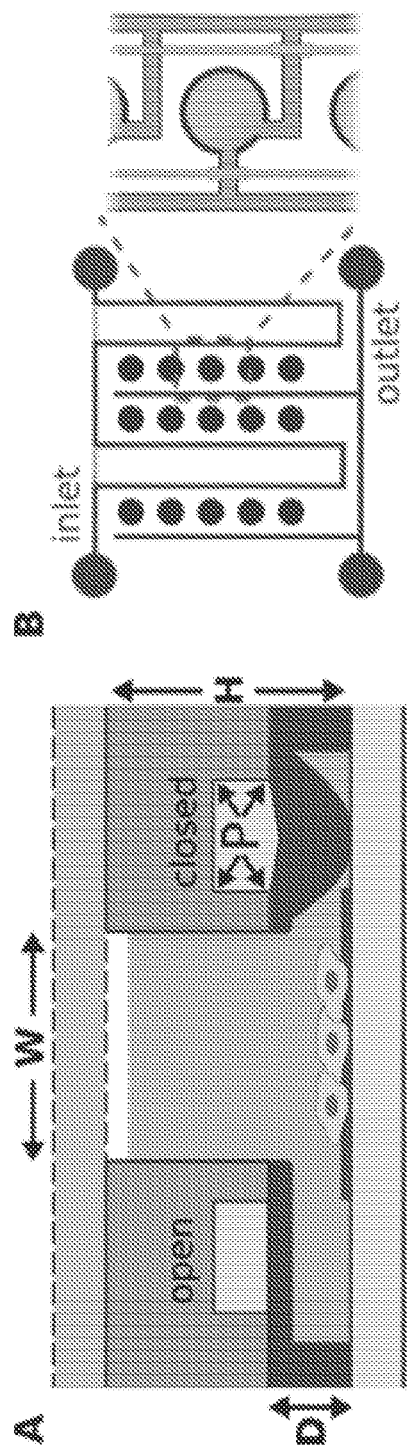
FIG. 2 is a diagram depicting a cross-sectional view (A) and top view (B) of a microfluidic device for use in the methods disclosed herein, in accordance with certain example embodiments.
Figure 3:
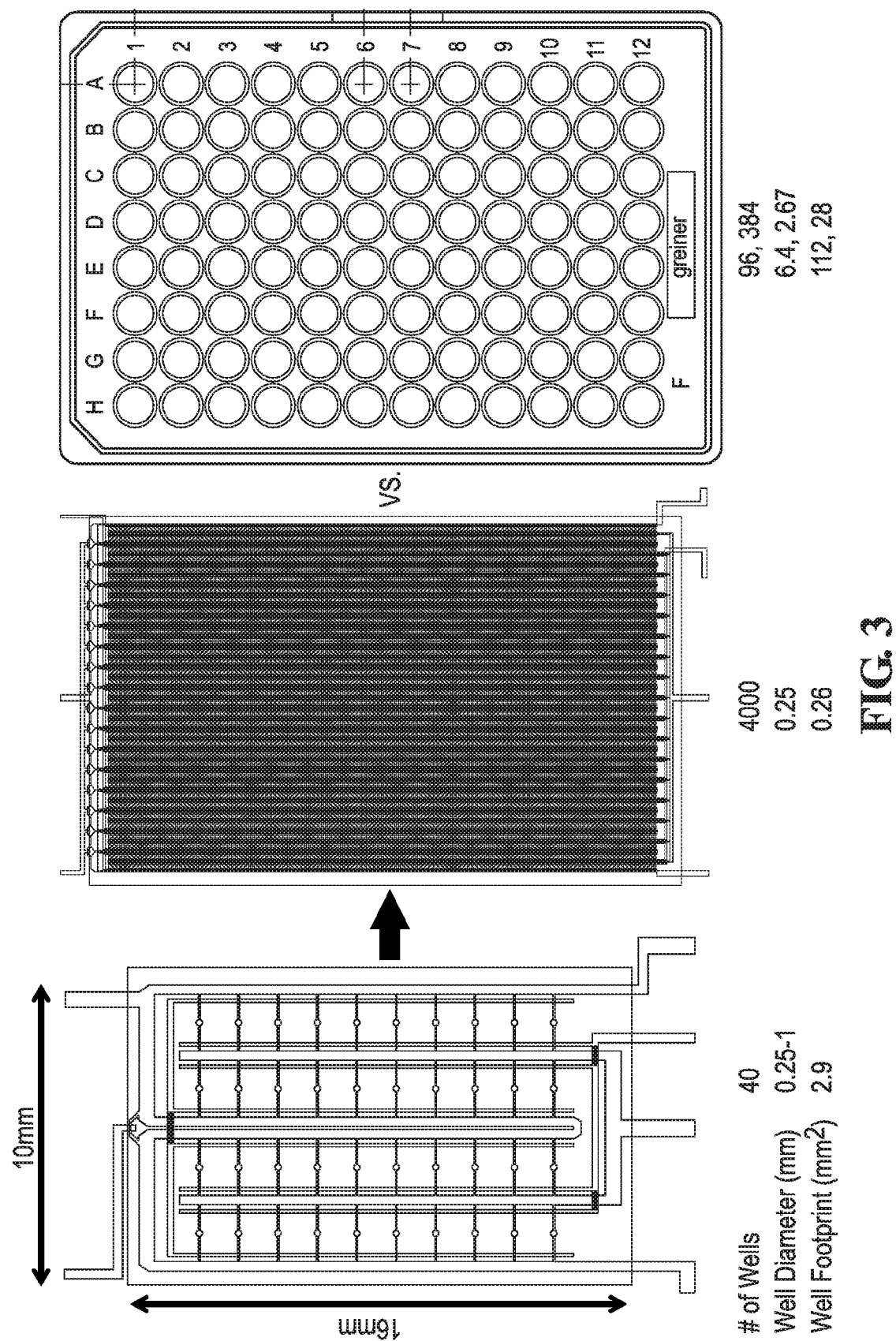
FIG. 3 is a diagram showing the scalability of the assay platforms for use with the methods disclosed herein, in accordance with certain example embodiments.

In certain example embodiments, the discrete volumes may be defined within a microfluidic device. An example device architecture is shown in FIGS. 2 and 3. The microfluidic device discrete volumes are defined as an array on an appropriate substrate. Each well comprises an input and an output in fluid communication with an input and output line. The inlet and outlet each have a valve that may be opened and closed independently of each other. The volume of the discrete volume may range from approximately 1 pL to approximately 1 µL. The number of discrete volumes defined on the microfluidic device may range from 1 to approximately 1 million.

Microfluidic devices disclosed herein may be silicone-based chips and may be fabricated using a variety of techniques, including, but not limited to, hot embossing, molding of elastomers, injection molding, LIGA, soft lithography, silicon fabrication and related thin film processing techniques. The microfluidic devices may be made of any material suitable for imaging of the discrete volumes using the imaging modalities described herein. Suitable materials for fabricating the microfluidic devices include, but are not limited to, cyclic olefin copolymer (COC), polycarbonate, poly(dimethylsiloxane) (PDMS), and poly(methylacrylate) (PMMA). In one embodiment, soft lithography in PDMS may be used to prepare the microfluidic devices. For example, a mold may be made using photolithogroaphy which defines the location of input/output lines, discrete volumes, inputs and outputs to discrete volumes, valves, and filters. The substrate material is poured into a mold and allowed to set to create a stamp. The stamp is then seal to a solid support, such as but not limited to, glass.

Due to the hydrophobic nature of some polymers, such as PDMS, which absorbs some proteins and may inhibit certain biological processes, a passivating agent may be necessary (Schoffner et al. Nucleic Acids Research, 1996, 24:375-379). Suitable passivating agents are known in the art and include, but are not limited to, silanes, parylene, n-Dodecyl-b-D-matoside (DDM), pluronic, Tween-20, other similar surfactants, polyethylene glycol (PEG), albumin, collagen, and other similar proteins and peptides The microfluidic devices may further comprise inlet and outlet ports, or openings, which in turn may be connected to valves, tubes, channels, chambers, and syringes and/or pumps for the introduction and extraction of fluids into and from the microfluidic device. The microfluidic devices may be connected to fluid flow actuators that allow directional movement of fluids within the microfluidic device. Example actuators include, but are not limited to, syringe pumps, mechanically actuated recirculating pumps, electroosmotic pumps, bulbs, bellows, diaphragms, or bubbles intended to force movement of fluids. In certain example embodiments, the microfluidic devices are connected to controllers with programmable valves that work together to move fluids through the microfluidic device. The microfluidic devices may be connected to flow actuators, controllers, and sample loading devices by tubing that terminates in metal pins for insertion into inlet ports on the microfluidic device. In certain example embodiments, the microfluidic devices may be sized to interface with existing instrumentation including spectrometer plate readers and microscopes for in situ monitoring and qualitative evaluation of culture conditions and outcomes.

Primers

To detect the nucleic acid sequence variations a set of nucleic acid primers are defined that can be used to amplify one or more target sequences comprising the nucleic acid sequence variation. The primers may comprise a specific target sequence binding region comprising nucleotides that are complimentary to a nucleic acid sequence near the target sequence. Alternatively, the primers may comprise a random sequence, such as a random hexamer, for random priming of the amplification reaction. One of ordinary skill in the art can select the appropriate primer and primer pairs based on the type of nucleic acid sequence variation to be assessed, and the nucleic acid sequence amplification reaction to be used.

Each primer is associated with and delivered to the discrete volumes by a particular type of optically encoded particle. To identify the optically encoded particle the primer is associated with, the primer sequence may include a particle identifier. The particle identifier is a short nucleic acid sequence that is mapped to a particular type of optically encoded particle. For example, the particle identifier may be a two, three, four, five, six, seven, or eight nucleic acid sequence that uniquely identifies a particular type of optically encoded particle. As one of skill in the art will understand, the size of the unique identifier will depend on the number of unique optically encoded particles that need to be identified. In certain example embodiments, the particle identifier may be incorporated at the 5' end of the primer. In certain example embodiments, the particle identifier sequences may be chosen to maximize edit distance amongst themselves, for example to allow for correction of PCR and sequencing error.

Each primer may be associated with an optically encoded particle by non-specific binding, e.g. adsorption and absorption, or specific binding. Specific binding of nucleic acids may be achieved using known methods in the art and will depend in part on the make-up of the optically encoded particle to which the nucleic acid is to be bound. In certain example embodiments, specific binding of the primer to the optically encoded particle may be facilitated by a particle binding sequence. The particle binding sequence may be added to the 5' end of the primer either next to the target sequence binding region of the primer or next to the particle identifier if present. The particle binding sequence is complimentary to an adapter sequence bound directly to the optically encoded particle. The particle binding sequence hybridizes to the adapter sequence to load the primer onto the optically encoded particle. In one embodiment, the primer is covalently linked to a particle, where the covalent linkage may be direct or indirect through the use of an intervening spacer or linker. Various types and lengths of the spacers and linkers are known in the art and choice will depend in part on the intended configuration and design and the various other components provided within the discrete volume.

Optically Encoded Particles

The optically encoded particles may be a particle of a particular size, shape, color, refractive index, or combination thereof. The particle should comprise a material and be of a size that can be resolvable as a discrete particle using light spectroscopy, non-linear optical microscopy, phase contrast microscopy, fluorescence microscopy, including two-photon fluorescence microscopy, Raman spectroscopy or a combination thereof. The particle must also be made of a material that is suitable for non-specific binding of primers, or amenable to surface modifications that allow for specific binding of primers. In certain example embodiments, the optically encoded particle may be naturally optically encoded, that is the particle is detectable using one of the above detection means without further modification. In certain other example embodiments, the particle material making up the optically encoded particle is amenable to modification such that it can be made optically detectable using one of the above detection means, for example, by fluorescently or colorimetrically labeling the particle. Finally, the particle should allow for efficient delivery of primers to the discrete volumes of the assay platform while not significantly interfering with the efficiency of the primers to bind and prime a nucleic acid amplification reaction. In one example embodiment, a particle that reduces the efficiency of the nucleic acid amplification reaction by approximately 1%, 5%, 10%, 15%, 20%, or 25% relative to a nucleic acid amplification reaction not carried out in the presence of the particle is considered to significantly interfere with the nucleic acid amplification reaction.

The optically encoded particles may comprise colloidal metal particles, nanoshells, nanotubes, nanorods, quantum dots, hydrogel particles, microspheres—such as polystyrene beads—liposomes, dendrimers, and metal-liposome particles. The optically encoded particles may be of any shape including, but not limited to, spherical, string-like, or rod-like. In certain example embodiments, the particles are spherical in shape. In certain example embodiments, the optically encoded particles may be formed in a series of pre-defined shapes or sizes in order to distinguish the optically encoded particles by shape or size. In certain example embodiments, the optically encoded particle may have a diameter of approximately 50 nm to approximately 500 µm, or a length of approximately 50 nm to 500 µm.

In one example embodiment, the particle is a hydrogel particle. The hydrogel particle may be made from, for example, covalently cross-linked PEG with thiol-reactive functional groups, or low melting point agarose functionalized with streptavidin or nucleic acid. In certain example embodiments, the hydrogel particle may be approximately 50 nm to approximately 500 µm in size. In certain example embodiments the hydrogel particle is fluorescently or colorimetrically labeled. In certain example embodiments, the optical label is incorporated within the hydrogel particle. In certain other example embodiments, the optical label is attached to the surface of the hydrogel particle.

In certain example embodiments, the optically encoded particles are quantum dots. In certain example embodiments, the quantum dots are associated with primers directly. In certain other example embodiments, the quantum dots may be incorporated into larger particles, such as those describe above, wherein the larger particles are then associated with primers. The quantum dots may be made of semiconductor materials identifiable in the art as suitable for forming quantum dots. Exemplary quantum dots are available for purchase, e.g., from Sigma-Aldrich. The quantum dots may range in size from approximately 2 nm to approximately 20 nm.

In certain example embodiments, the optically encoded particle is a colloidal metal particle. The colloidal metal material may include water-insoluble metal particles or metallic compounds dispersed in a liquid, a hydrosol, or a metal sol. The colloidal metal may be selected from the metals in groups IA, IB, IIB and IIIB of the periodic table, as well as the transition metals, especially those of group VIII. Preferred metals include gold, silver, aluminum, ruthenium, zinc, iron, nickel and calcium. Other suitable metals also include the following in all of their various oxidation states: lithium, sodium, magnesium, potassium, scandium, titanium, vanadium, chromium, manganese, cobalt, copper, gallium, strontium, niobium, molybdenum, palladium, indium, tin, tungsten, rhenium, platinum, and gadolinium. The metals are preferably provided in ionic form, derived from an appropriate metal compound, for example the $Al^{3+}$, $Ru^{3+}$, $Zn^{2+}$, $Fe^{3+}$, $Ni^{2+}$ and $Ca^{2+}$ ions.

In certain example embodiments, the optically encoded particles are dendrimers. The dendrimer may be formed using standard methods known in the art. Exemplary dendrimers are available for purchase, e.g., from Sigma-Aldrich. The dendrimer may range in size from 5 nm to 500 nm, depending on the chosen size and length of, e.g., a central core, an interior dendritic structure (the branches), and an exterior surface with functional surface groups.

In certain example embodiments, the optically encoded particles are microspheres. The microspheres may be made using standard methods known in the art. In certain example, embodiments the microspheres are dyed different colors. In certain example embodiments, the microspheres may range in size from approximately 50 nm to approximately 500 µm.

The number of distinct optical barcodes in a given set will depend on the number of distinguishable optical particles that are available for that particular imaging modality. For example, Table 1 provides the number of distinct fluorescent optical particles available given a certain number of distinguishable fluorescent intensities and the number of fluorescent dyes used. The first number removes resulting particles that are identical after normalization to the brightest intensity.

TABLE 1

| | Distinct codes: ratiometric (all) | | | | |
|---|---|---|---|---|---|
| | 2 levels | 3 levels | 4 levels | 5 levels | 6 levels |
| 2 dyes | 3 (3) | 5 (8) | 9 (15) | 13 (24) | 21 (35) |
| 3 dyes | 7 (7) | 19 (26) | 49 (63) | 91 (124) | 175 (215) |
| 4 dyes | 15 (15) | 65 (80) | 225 (255) | 529 (624) | 1185 (1295) |
| 5 dyes | 31 (31) | 211 (242) | 961 (1032) | 2851 (3124) | . . . |

In certain example embodiments, the set of optically encoded particles comprises up to 500, up to 300, up to 200, up to 100, up to 50 or up to 40 distinct optically encoded particles. In one example embodiment, the set of optically encoded particles may comprise 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 35, or 37 distinct optically encoded particles. In one example embodiment, a total of six distinct optically encoded particles is used. In another example embodiment, a total of seven distinct optically encoded particles is used. In another example embodiment, a total of eight distinct optically encoded particles is used. In another example embodiment, a total of nine distinct optically encoded particles is used. In another example embodiment, a total of ten distinct optically encoded particles is used. In one embodiment, each distinct type of particle within the set of encoded particles may further comprise one or more unique nucleic acid particle identifier that are associated only with that distinct particle type within the set. In one embodiment, each distinct type of particle within the set of encoded particles may further comprise one or more unique nucleic acid primers that are associated only with that distinct particle type within the set. Random or assigned combinations of a given number of particles from each set may be delivered and/or assigned to each discrete volume, wherein detection of the unique combination of particles identifies that discrete volume, and association of the particle identifier included in the aligned sequence information, as discussed further below, allows one skilled in the art to assign the data parameters back to the discrete volume where that particular combination was originally assigned.

Distribution of Optically Encoded Particles

The set of primer-loaded optically encoded particles may be combined into one or more solutions. The one or more solutions are then introduced to the discrete volumes such that the optically encoded particles are distributed across the discrete volumes. In certain example embodiments, the optically encoded particles are assigned to each discrete volume. In certain other example embodiments, the optically encoded particles are randomly distributed to each discrete volume. In certain other example embodiments, the set of optically encoded particles are combined into a single solution and randomly distributed to the discrete volumes. Accordingly, in such an embodiment each discrete volume receives a random subset of optically encoded particles loaded with one or more primers as discussed above. Random distribution of the optically encoded particles may be achieved by pumping, mixing, rocking, or agitation of the assay platform for a time sufficient to allow for distribution to all discrete volumes. One of ordinary skill in the art can select the appropriate mechanism for randomly distributing the optically encoded particles across discrete volumes based on the assay platform used.

Imaging of Discrete Volumes

In one embodiment, the assigned or random subset(s) of beads received in each discrete volume dictates the observable pattern of discrete optically encoded particles in each discrete volume thereby allowing each discrete volume to be independently identified. Each discrete volume is imaged with the appropriate imaging technique to detect the optically encoded particles. For example, if the optically encoded particles are fluorescently labeled each discrete volume is imaged using a fluorescent microscope. In another example, if the optically encoded particles are colorimetrically labeled each discrete volume is imaged using a microscope having one or more filters that match the wave length or absorption spectrum or emission spectrum inherent to each color label. Other detection methods are contemplated that match the optical system used, e.g., those known in the art for detecting quantum dots, dyes, etc. The pattern of observed discrete optically encoded particles for each discrete volume may be recorded for later use.

In addition, optical assessments of each nucleic acid containing species in each discrete volume are made. For example, if the nucleic acid containing species is a cell, the phenotype of the cell may be observed via optical imaging of the discrete volumes. Optical assessments may be recorded for later use. In one embodiment, observable cell phenotypes may include changes in morphology, motility, and cell death. Optical assessments may also include cell-cell contact, such as but not limited to antigen presentation and synapsing, and interaction with a patterned substrate such as, but not limited to, patterned extracellular matrix proteins. In certain example embodiments, an additional imaging agent may be delivered to cells. For example dyes or stains that label certain sub-cellular components such as the nucleus, cytoskeleton, endoplasmic reticulum, mitochondria, or cell wells. In addition, molecule-specific labeling agents such as labeled antibodies or labeled nucleic acids may be used to track changes in localization of certain target molecules. In one embodiment, acellular systems may be assessed using optical assays for protein:protein interactions, quantitation of components of interest, enzymatic activity, and the like.

Nucleic Acid Amplification and Sequencing

In one embodiment, one or more target sequences comprising the nucleic acid sequence variation to be screened is amplified using a nucleic acid amplification reaction. The type of amplification reaction used will depend on the type of nucleic acid primers delivered via the optically encoded particles. Example nucleic acid amplification reactions that may be used include PCR, RT-PCR (for RNA), whole genome amplification (WGA), loop-mediated isothermal amplification (LAMP), linear amplification, rolling circle amplification, strand displacement amplification or other nucleic acid amplification reactions known in the art, and combinations of these amplification methods. In one example embodiment, the primer particle identifier is incorporated in the generated amplicons. After generation of the amplicon comprising the target sequence, all amplicons may be collected as a single sample from the assay platform device and sequenced using, for example, next generation sequencing (NGS) techniques known in the art.

The sequenced amplicons may then be clustered by sequence similarity of the one or more target sequences. Alignment by sequence variation will allow for identification of optically encoded particles delivered to a discrete volume based on the particle identifiers incorporated in the aligned sequence information. For example, as shown in FIG. 1, the delivery of three forward primers associated with three distinct optically encoded particles, and delivery of three reverse primers associated with three distinct optically encoded particles will result in amplicons comprising the same sequence variation but incorporating different combinations of forward and reverse primers. In one embodiment, the particle identifier of each primer incorporated in the aligned sequence information indicates the pattern of optically encoded particles that is observable in the corresponding discrete volume from which the amplicons are generated. In this way the nucleic acid sequence variation can be correlated back to the originating discrete volume and further matched to the optical assessments, such as phenotype, made of the nucleic acid containing specimens in that discrete volume.

Engineered Genetic Perturbations

In certain example embodiments, nucleic acid variations to be screened are engineered genetic perturbations. In certain example embodiments, a library comprising the genetic perturbations to be screened is generated. For example, the library may contain a set of plasmids or other suitable delivery vector with each delivery vector comprising one or more genetic perturbations. The genetic perturbation may include a gene knock-in, a gene knock-out, or one or more nucleotide insertions, deletions, or substitutions. The engineered genetic perturbation may be generated using, for example, CRISPER/Cas9, RNAi (siRNA and shRNA), TALEN, Zn Finger enzymes, site directed mutagenesis, or other genetic engineering methods known in the art, or a combination thereof. The delivery vectors are then used to introduce the genetic perturbation into one or more nucleic sequences of the nucleic acid containing specimen prior to, or subsequent to, loading the nucleic acid containing specimens into the discrete volumes. As noted above, the nucleic acid containing specimens may be exposed to different physical parameters, such as temperature and pressure, or different chemical perturbations, such as exposure to different types or concentrations of a therapeutic agent, or a combination thereof. For example, the methods described herein may be used to see the effect certain therapeutic agents have, such as cell death, in the different genetic context introduced by the genetic perturbations.

The invention is further described in the following examples, which do not limit the scope of the invention described in the claims.

EXAMPLES

Example 1—Detection of Individual Fluorescently-Labeled Particles

DNA-functionalized particles were synthesized from PEG hydrogel precursors and subsequently labeled with distinct rations of the dyes FAM, Cy3 and Cy5. The main hydrogel chemistry used was a mixture of 4-arm PEG with acrylate groups and dithiol PEG. Adapter oligos containing a 5' thiol were mixed with dithiol PEG, and the two PEG forms were mixed in a coflow microfluidic emulsion generator immediately prior to forming droplets in fluorinated oil in a mildly basic buffer. After an incubation of 45 min, the gel-in-oil droplets were removed from oil by electrocoalescence, washed, and transferred to an annealing buffer containing a mixture of dye-labeled oligos and barcoded primers. After annealing, the hydrogel particles now bearing primers with barcode sequence and fluorescent oligos in corresponding color ratio were washed several times by centrifugation and stored either at 4° C. for usage within 3 days or at −20° C. for usage at a later date. An alternate chemistry was used to attach adapter oligos directly to ultra low melting point agarose via Schiff base addition. The dye ratios were chosen so that after normalization to FAM intensity the dyes are evenly spaced in logarithmic coordinates.

Figure 4:
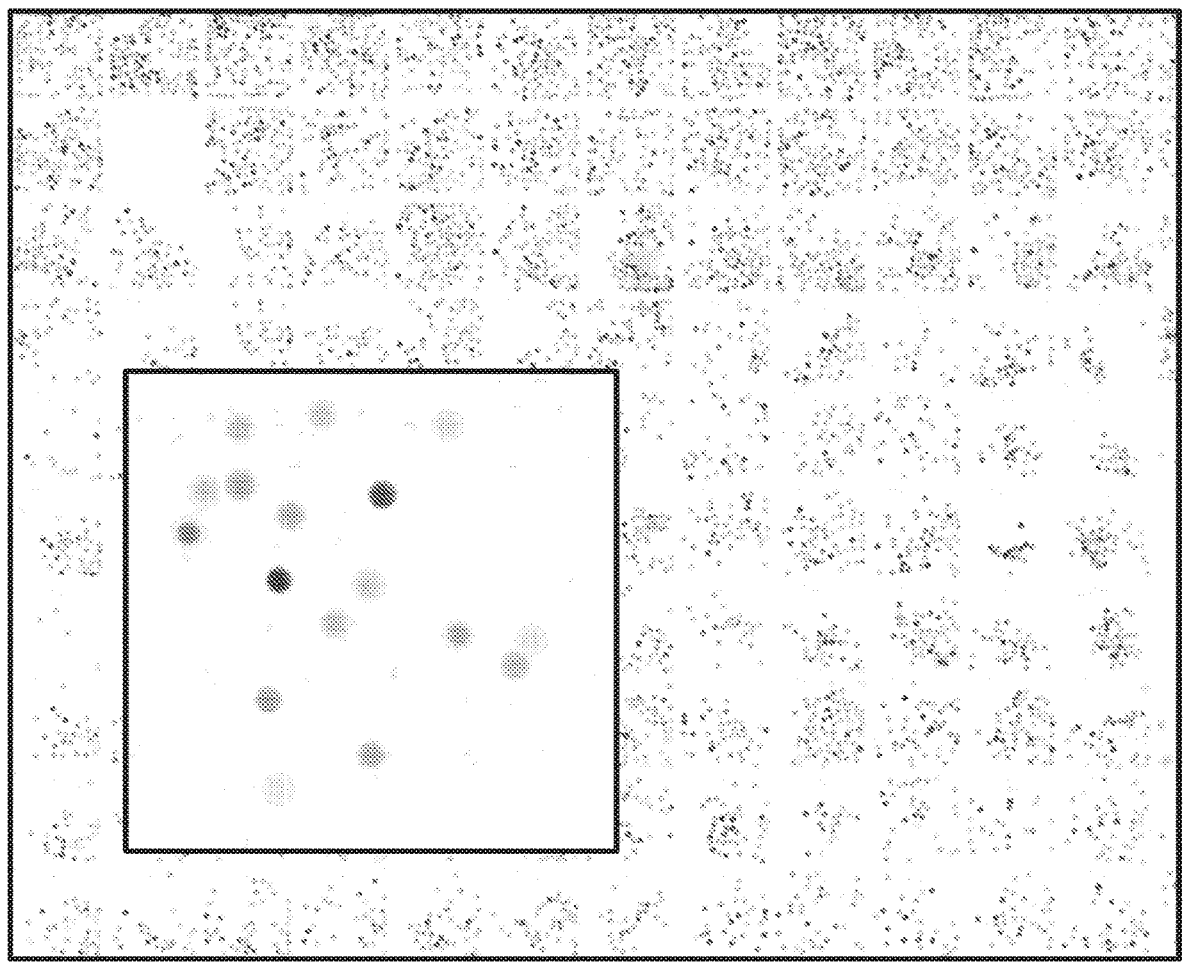
FIG. 4 is an image of observed optically encoded particles randomly deposited into individual wells of a 384 microwell plate with the insert depicting the optically encoded particles delivered to a single well.

Labeled particles were randomly deposited into a 384 well microplate and imaged. Shown in FIG. 4 is a three color overlay of fluorescence images acquired in FAM, Cy3, and Cy5 channels. The inset depicts a single well from the microplate and demonstrates the ability to detect unique combinations of discrete fluorescently labeled particles across individual discrete volumes when the optically encoded particles are distributed randomly.

Figure 5:
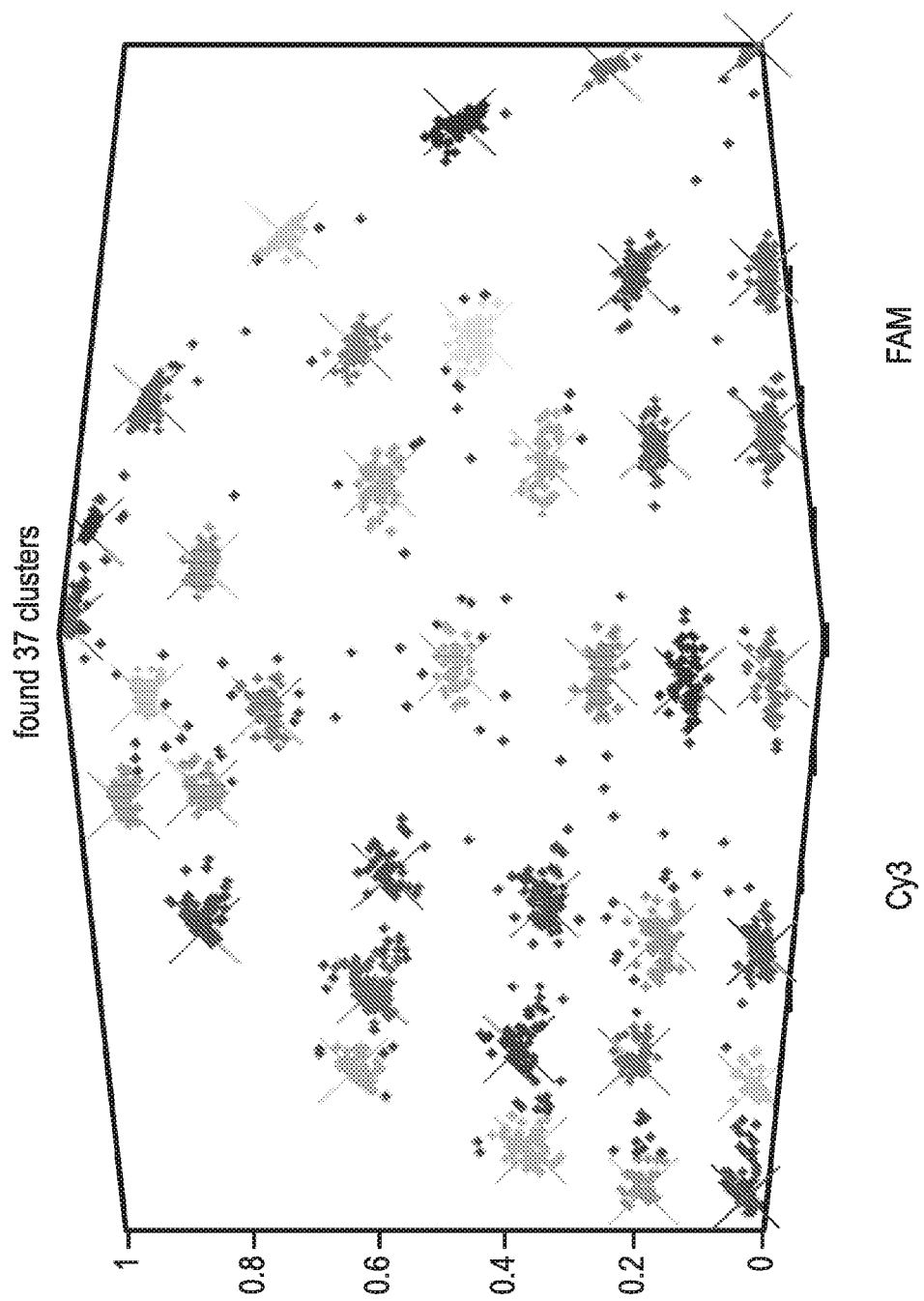
FIG. 5 is a graph showing the detection of 37 differently colored optically encoded particles. The particles were encoded with different ratios of fluorescent dyes and randomly distributed in the wells of a 384 well microplate prior to detection.

After computational filtering, detected particles in the 384 wells were clustered in an unsupervised fashion using the DBSCAN algorithm. This algorithm detected 37 distinct groups of particles, plus outliers belonging to no groups. See FIG. 5. The 37 groups found matches exactly the 37 differently-colored types of particles used in the experiment.

Figure 6:
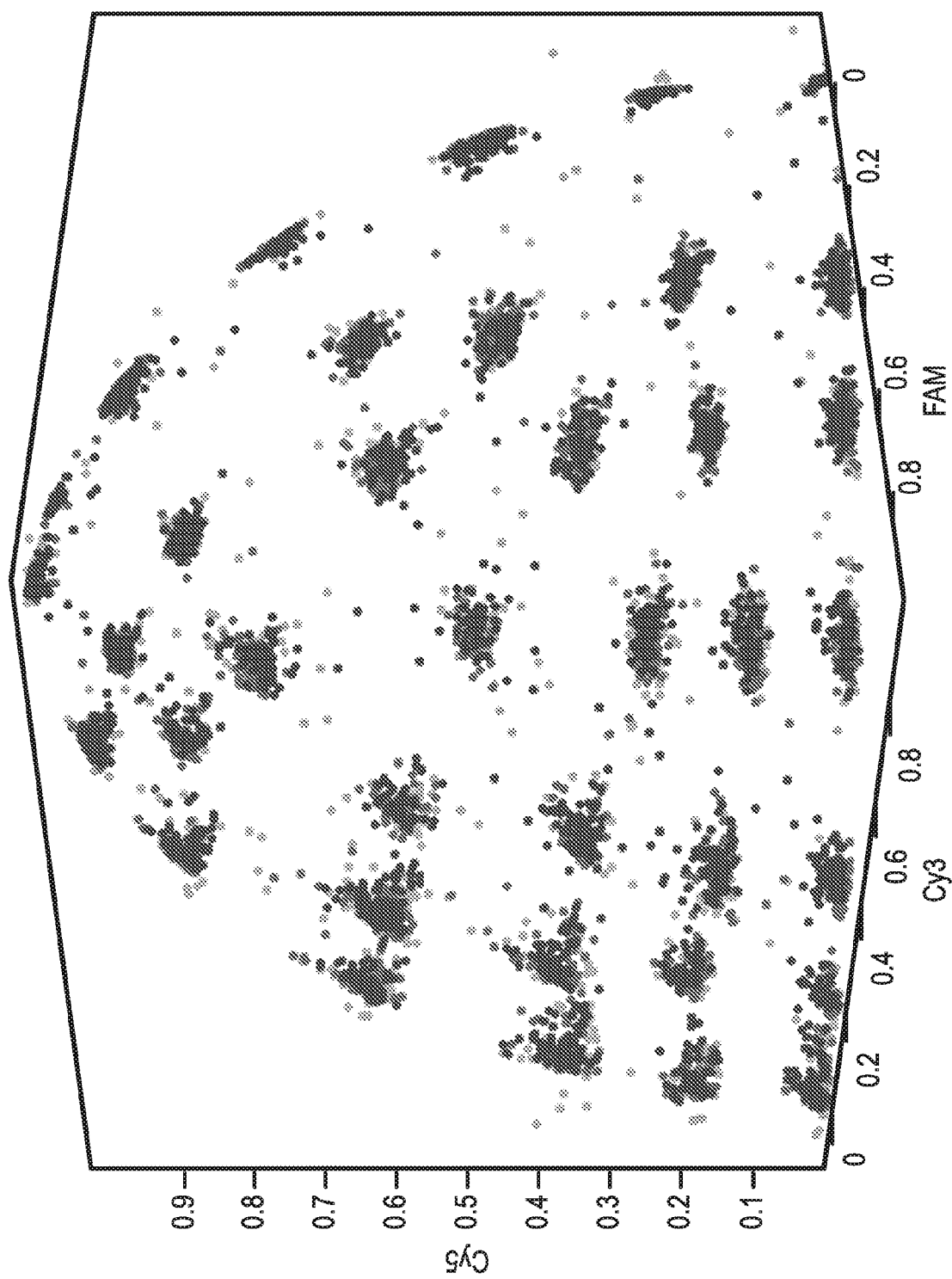
FIG. 6 is a graph showing points corresponding to detected particles in a 384 well plate before and after two rounds of vortexing, demonstrating the observed clustering is robust to the placement of particles in the imaging plane.

Referring to FIG. 6, after imaging the color-coded particles in the 384 microwell plate, the plate was vortexed for 60 seconds then briefly centrifuged to randomize the particle positions in each well. Points shown in blue, green, and red correspond to detected particles before vortexing and after two rounds of vortexing. This demonstrates that the clustering is robust to random variation in the placement of the particles in the imaging plane.

Figure 7:
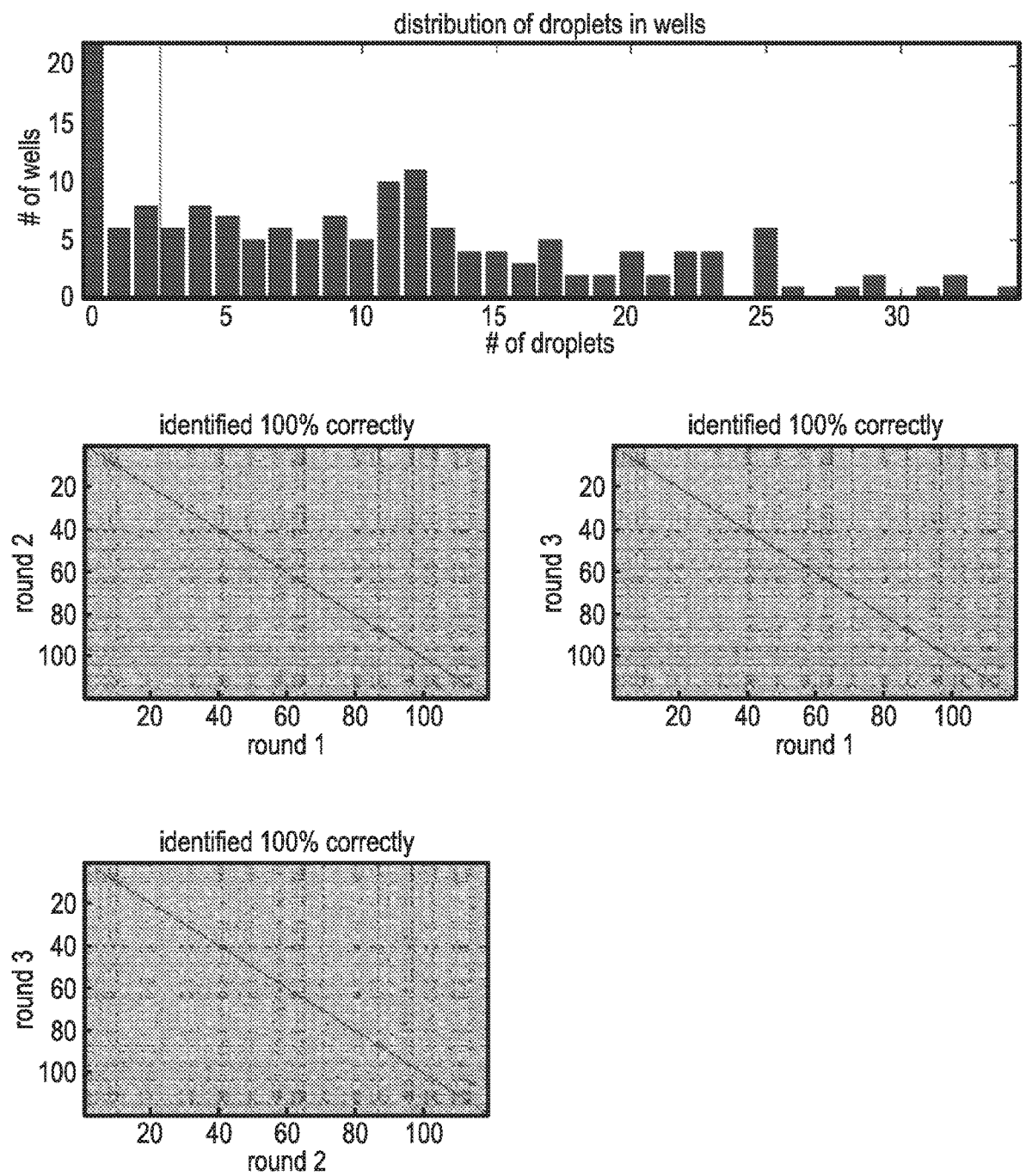
FIG. 7 is a set of graphs showing the distribution of differently colored optically encoded particles in each well (top) and the correct identification of each well based on the number and color of optical particles observed after three separate rounds of vortexing (bottom).

Referring to FIG. 7, to test whether well identity assignments are robust to variation in the spatial distribution of particles, the data from before and after two rounds of vortexing was used to recover well identity. After randomizing well identity in each round, the Hungarian algorithm was used to optimally assign identity between wells containing at least one droplet across rounds (heat maps, bottom). This approach found the known well identities with 100% accuracy in all cases. Thus, well identification is highly robust to differences in the number of particles loaded per well, demonstrated by the perfect identification despite the broad range in droplets loaded per well (histogram, top).

What is claimed is:

1. A method for multiplex screening of nucleic acid sequence variations comprising:
    loading a nucleic acid-containing specimen comprising one or more nucleic acid sequence variations into one or more discrete volumes;
    dispensing one or more solutions across all discrete volumes, the solution comprising a set of optically-encoded particles, each particle having one or more primers of a same primer type associated therewith, and each primer of the same primer type comprising a same particle identifier that identifies a type of optically-encoded particle the primer is associated with;
    detecting a combination of optically-encoded particles delivered to each discrete volume and recording the combination of optically-encoded particles observed in each discrete volume;
    generating amplicons in each discrete volume using the one or more primers delivered to each discrete volume by the optically-encoded particles, wherein the one or more primers amplify one or more target sequences comprising the nucleic acid sequence variation to be screened;
    sequencing the generated amplicons from each discrete volume, wherein the amplicon sequence information includes the primer particle identifier;
    clustering the generated amplicon sequence data by sequence similarity of the one or more target sequences; and
    determining the discrete volume in which the cluster of amplicon sequences originated by matching the particle identifiers from the cluster of amplicon sequences to the discrete volume where a corresponding combination of optically-encoded particles was detected.

2. The method of claim 1, further comprising:
    making optical assessments of the nucleic acid-containing specimen in each discrete volume by capturing an image of each discrete volume; and
    correlating the amplicon sequence information to the observed optical assessment based at least in part on the determining step.

3. The method of claim 1, wherein all the generated amplicons are pooled from all discrete volumes and bulk sequenced using a next-generation sequencing method.

4. The method of claim 1, wherein the amplicons are generated using PCR, RT-PCR, whole genome amplification, loop-mediated isothermal amplification, linear amplification, rolling circle amplification, strand displacement amplification or a combination thereof.

5. The method of claim 1, wherein the nucleic acid-containing specimen is one or more cells.

6. The method of claim 5, wherein the one or more cells are derived from a tissue sample of a subject.

7. The method of claim 1, wherein the nucleic acid sequence variation to be screened is natural genetic sequence variability, gene expression variability, engineered genetic perturbations, or a combination thereof.

8. The method of claim 7, wherein the engineered genetic perturbation is a gene knock-in, a gene knock-out, or one or more nucleotide insertions, deletions, or substitutions.

9. The method of claim 8, wherein the engineered genetic perturbation is generated using CRISPR/Cas9, RNAi, TALEN, or Zn finger enzymes.

10. The method of claim 1, further comprising exposing the nucleic acid-containing specimen in each discrete volume to a same agent or combination of agents, or different agent or combination of agents.

11. The method of claim 10, wherein the agent is a therapeutic agent.

12. The method of claim 1, wherein each of the optically-encoded particles is a particle of a unique size, shape, refractive index, color, or combination thereof.

13. The method of claim 1, wherein each of the optically-encoded particles comprise colloidal metal particles, nanoshells, nanotubes, nanorods, quantum dots, hydrogel particles, liposomes, dendrimers, or metal-liposome particles.

14. The method of claim 13, wherein the hydrogel particle is labeled with one or more fluorophores.

15. The method of claim 1, wherein each of the optically-encoded particles is detected using light microscopy, fluorescence microscopy, Raman spectroscopy, or a combination thereof.

16. The method of claim 1, wherein each of the optically-encoded particles is approximately 50 nm to approximately 500 µm in size.

17. The method of claim 1, wherein the set of optically-encoded particles comprises 2 to 500 optically-encoded particles, optionally 10 optically-encoded particles.

18. The method of claim 1, wherein each of the optically-encoded particles further comprises an adapter binding element which binds to an adapter sequence on the one or more primers.

19. The method of claim 1, wherein the discrete volumes are wells of a multi-well plate.

20. The method of claim 1, wherein the discrete volumes are defined on a microfluidic chip.

21. The method of claim 20, wherein the microfluidic chip defines between 1 and 1 million discrete volumes.

22. The method of claim 20, wherein the discrete volumes are defined in rows in the microfluidic chip and wherein each discrete volume in each row is connected to a common inlet fluid channel and a common outlet flow channel.

23. The method of claim 22, wherein each discrete volume has an inlet valve at the interface with the inlet fluid channel and an outlet valve at the interface of the outlet channel that can be independently opened and closed.

* * * * *

UNITED STATES PATENT AND TRADEMARK OFFICE
CERTIFICATE OF CORRECTION

PATENT NO. : 11,421,270 B2
APPLICATION NO. : 15/754984
DATED : August 23, 2022
INVENTOR(S) : Feldman et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 642 days.

Signed and Sealed this
Twenty-eighth Day of January, 2025

Coke Morgan Stewart
*Acting Director of the United States Patent and Trademark Office*